(12) United States Patent
Cohen et al.

(10) Patent No.: US 11,301,879 B2
(45) Date of Patent: Apr. 12, 2022

(54) SYSTEMS AND METHODS FOR QUANTIFYING CUSTOMER ENGAGEMENT

(71) Applicant: Aktana, Inc., San Francisco, CA (US)

(72) Inventors: Marc Cohen, San Francisco, CA (US); Anna Decker, San Francisco, CA (US)

(73) Assignee: AKTANA, INC., San Francisco, CA (US)

( * ) Notice: Subject to any disclaimer, the term of this patent is extended or adjusted under 35 U.S.C. 154(b) by 0 days.

(21) Appl. No.: 16/554,529

(22) Filed: Aug. 28, 2019

(65) Prior Publication Data

US 2020/0027100 A1 Jan. 23, 2020

Related U.S. Application Data

(63) Continuation of application No. PCT/US2019/023263, filed on Mar. 20, 2019.

(60) Provisional application No. 62/646,070, filed on Mar. 21, 2018.

(51) Int. Cl.
G06Q 30/02 (2012.01)
G16H 20/10 (2018.01)
G16H 80/00 (2018.01)

(52) U.S. Cl.
CPC ..... G06Q 30/0201 (2013.01); G06Q 30/0204 (2013.01); G16H 20/10 (2018.01); G16H 80/00 (2018.01)

(58) Field of Classification Search
CPC .... G06Q 10/00; G06Q 30/02; G06Q 30/0201; G06Q 30/0204; G06Q 30/0205; G06Q 10/0637; G06Q 10/0639
USPC ................................................ 705/7.11–7.42
See application file for complete search history.

(56) References Cited

U.S. PATENT DOCUMENTS

| 6,842,736 B1 | 1/2005 | Brzozowski |
| 9,760,925 B2 | 9/2017 | Petrimoulx et al. |
| 2006/0190288 A1* | 8/2006 | Boardman ......... G06Q 30/0205 705/7.31 |

(Continued)

FOREIGN PATENT DOCUMENTS

JP 2015043194 A 3/2015

OTHER PUBLICATIONS

Trucco et al., Transforming Pharmaceutical Marketing Through e-detailing: Case Studies and Recommendations, Jan. 1, 2006, IEEE 3rd IEEE International Conference on Enterprise Computing, E-Commerce, and E-Services, pp. 1-7 (Year: 2006).*

(Continued)

*Primary Examiner* — Robert D Rines
(74) *Attorney, Agent, or Firm* — Wilson Sonsini Goodrich & Rosati

(57) ABSTRACT

A health care provider (HCP) engagement engine is disclosed. The HCP engagement engine facilitates effective communication between pharmaceutical sales representatives (pharma reps) and HCPs by tracking actions performed by pharma reps to sell products to HCPs, analyzing the actions, and eliminating confounding effects due to inbound and outbound activities. Inbound activities include behaviors performed by pharma reps to the HCPs, while outbound activities are taken by HCPs in response to the inbound activities. Reducing confounding allows the pharma reps to have better information about which behaviors best drive HCP engagement.

21 Claims, 10 Drawing Sheets

(56) References Cited

U.S. PATENT DOCUMENTS

| | | | |
|---|---|---|---|
| 2006/0190311 A1* | 8/2006 | Boardman | G06Q 30/0205 705/7.34 |
| 2009/0281868 A1* | 11/2009 | Spanbauer | G06Q 10/0639 705/7.33 |
| 2012/0215554 A1 | 8/2012 | Yurkovich | |
| 2013/0006711 A1* | 1/2013 | Biswas | G06Q 30/02 705/7.33 |
| 2014/0019237 A1* | 1/2014 | Gottfrid | G16H 20/10 705/14.52 |
| 2014/0278507 A1 | 9/2014 | Potter | |
| 2019/0066830 A1* | 2/2019 | Kumar | G16H 80/00 |

OTHER PUBLICATIONS

PCT/US2019/023263 International Search Report and Written Opinion dated Jul. 22, 2019.
EP19772482.6 Extended European Search Report dated Nov. 29, 2021.

\* cited by examiner

SYSTEMS AND METHODS FOR QUANTIFYING CUSTOMER ENGAGEMENT

CROSS-REFERENCE

This application is a continuation application of International Application PCT/US19/23263, filed on Mar. 20, 2019, which application claims the benefit of U.S. Provisional Patent Application No. 62/646,070 filed Mar. 21, 2018 which is incorporated herein by reference in its entirety.

BACKGROUND

To provide products and services to health care providers (HCPs) more effectively, pharmaceutical sales representatives (pharma reps) have to communicate and engage with the HCPs in a more targeted manner. Effective communications may include in-person meetings, telephone calls, and networking opportunities. It is in the pharma reps' best interests to collect as much data about interactions with HCPs as possible, in order to improve their interactions with the HCPs and thus generate more sales.

Retrieval and analysis of sales and marketing data may present certain challenges. For example, sales data may be available only at an aggregate level. Data from individual HCPs may not be readily available. Some customer resource management (CRM) software may collect HCP data, but may not collect individualized data or may obscure particular data entries for privacy reasons. Additionally, HCP data, for example, prescription data, may be provided at a facility level, or into "bricks", which can make it difficult to parse successful sales to specific HCPs. In addition, pharmaceutical sales resulting from HCP prescriptions or recommendations may be affected by variables outside of specific pharma rep interactions. These confounding variables can make it difficult to determine the effects of specific actions within (as well as outside of) the control of the pharma rep or a pharmaceutical company. Difficulty in collecting and analyzing data, along with various confounding variables, may cause the company's efforts to be potentially misdirected and the salesperson's efficiency to be reduced.

SUMMARY

In order to better understand the efficacy of targeted actions from pharmaceutical sales reps (pharma reps) to healthcare providers (HCPs), there is a need for methods and systems that can mitigate the effects of brick data collection and mitigate the effects of confounding variables. The systems and methods disclosed herein can compensate for the effects of confounding variables, by adjusting brick-level sales data using information collected from pharma reps and HCPs. The disclosed systems and methods can perform operations on the adjusted sales data to remove the effects of the confounding variables.

In one aspect, a computer-implemented method is disclosed. The method may comprise obtaining data from a plurality of data sources. The data may comprise (1) aggregate sales values of a pharmaceutical product and (2) a plurality of attributes comprising (i) information associated with a plurality of healthcare facilities and (ii) information associated with a plurality of healthcare providers (HCPs). The plurality of HCPs may be provided under a plurality of bricks with each brick comprising one or more of the healthcare facilities and each facility comprising one or more HCPs. The method may comprise generating the adjusted sales data by distributing the aggregate sales values across the HCPs that are within each brick for the plurality of bricks.

In some embodiments, the plurality of data sources may comprise multiple databases for customer resource management (CRM), market segmentation, sales, and/or a pharmaceutical company's proprietary databases.

In some embodiments, the plurality of bricks may be defined based on one or more factors including geographical region, location of a facility, size of a facility, number of HCPs within a facility, socioeconomics of a region, demographics of a region, or other non-geographical factor(s).

In some embodiments, the plurality of bricks may comprise a first group of bricks and a second group of bricks. Each brick in the first group of bricks may comprise a distinct collection of healthcare facilities. Each brick in the second group of bricks may comprise a single distinct healthcare facility.

In some embodiments, the adjusted sales data may comprise sales values that are disaggregated at an individual HCP level instead of at a brick level.

In some embodiments, the method may further comprise using the adjusted sales data as a target in a predictive model to estimate impacts of different marketing strategies on the sales of the pharmaceutical product.

In some embodiments, the method may further comprise identifying, based on the estimated impacts of the different marketing strategies, one or more marketing strategies to optimize the sales of the pharmaceutical product.

In some embodiments, the method may further comprise providing recommendations of the one or more identified marketing strategies to a user. The user may include one or more sales representatives for the pharmaceutical product.

In some embodiments, the recommendations may be provided as one or more graphical visual objects configured to be displayed on an electronic device associated with the user.

In some embodiments, the aggregate sales values may be distributed across the HCPs based in part on an outbound activity data of the HCPs in the corresponding brick.

In some embodiments, the outbound activity data may be associated with one or more actions taken by the HCPs that are not a direct result of specific actions taken by an entity that is selling the pharmaceutical product.

In some embodiments, the outbound activity data may comprise a plurality of outbound features comprising (1) a number of visits by the HCPs to webpages of a company that is offering the pharmaceutical product for sale, (2) a number of communications from the HCPs to one or more sales representatives for the pharmaceutical product, (3) a number of relevant symposiums attended by the HCPs, or (4) a number of endorsements by the HCPs of the pharmaceutical product or other similar HCP actions.

In some embodiments, the aggregate sales values may be distributed across the HCPs within each brick by projecting the aggregate sales values onto a space defined by the outbound activity.

In some embodiments, the aggregate sales values may be projected onto the space using a linear transformation or a non-linear transformation.

In some embodiments, a subset of the plurality of outbound features may be functions of, or related to each other.

In some embodiments, a subset of the plurality of outbound features may be functions of, or related to one or more of the attributes.

In some embodiments, a plurality of weights may be applied to a plurality of outbound features associated with the outbound activity. A higher weight may be applied to a first outbound feature having a higher value or importance, and a lower weight may be applied to a second outbound feature having a lower value or importance.

In some embodiments, the outbound activity may be provided as an outbound matrix comprising (1) a plurality of outbound features as columns in the matrix and (2) the individual HCPs in the brick as rows in the matrix.

In some embodiments, the adjusted sales data may be generated based on (1) a pseudoinverse of the outbound matrix and (2) an average brick level sales per HCP in the brick.

A system is disclosed in another aspect of the disclosure. The system may comprise a server in communication with a plurality of data sources; and a memory storing instructions that, when executed by the server, cause the server to perform a set of operations. The operations may comprise obtaining data from the plurality of data sources. The data may comprise (1) aggregate sales values of a pharmaceutical product and (2) a plurality of attributes comprising (i) information associated with a plurality of healthcare facilities and (ii) information associated with a plurality of healthcare providers (HCPs). The plurality of HCPs may be provided under a plurality of bricks with each brick comprising one or more of the facilities and each facility comprising one or more HCPs. The operations may also include generating an adjusted sales data by distributing the aggregate sales values across the HCPs that are within each brick for the plurality of bricks.

In a further aspect, a non-transitory computer readable storage medium is disclosed. The storage medium may include instructions that, when executed by a server, cause the server to perform a set of operations. The operations may comprise obtaining data from a plurality of data sources. The data may comprise (1) aggregate sales values of a pharmaceutical product and (2) a plurality of attributes comprising (i) information associated with a plurality of healthcare facilities and (ii) information associated with a plurality of healthcare providers (HCPs). The plurality of HCPs may be provided under the plurality of bricks with each brick comprising one or more of the healthcare facilities and each facility comprising one or more HCPs. The operations may also include generating an adjusted sales data by distributing the aggregate sales values across the HCPs that are within each brick for the plurality of bricks.

In another aspect, a computer-implemented method for estimating an impact of inbound activity on sales of a pharmaceutical product is provided. The method may comprise obtaining data from a plurality of data sources. The data may comprise (1) information associated with a plurality of healthcare providers (HCPs) and (2) inbound activity data associated with events or actions taken (a) by one or more sales representatives or (b) an automated marketing system relating to the sales of the pharmaceutical product. The method may further comprise estimating effects of the inbound activity data on the sales of the pharmaceutical product to the plurality of HCPs by using adjusted sales data as a first target in a predictive model. The adjusted sales data may be obtained by distributing aggregate sales values across the HCPs that are within each brick for a plurality of bricks associated with the plurality of HCPs.

In some embodiments, the method may further comprise ranking a plurality of inbound features based on the estimated effects of the inbound activity data. The ranking may be indicative of an importance or dominance of each of the plurality of inbound features.

In some embodiments, a plurality of weights may be applied to a plurality of inbound features in the inbound activity data. A higher weight may be applied to a first inbound feature having a higher value or importance, and a lower weight may be applied to a second inbound feature having a lower value or importance.

In some embodiments, a plurality of inbound features in the inbound activity data may comprise (1) a number of visits by the one or more sales representatives to the HCPs, (2) a number of electronic communications sent by the one or more sales representatives to the HCPs, (3) a number of telephone calls from the one or more sales representatives to the HCPs, (4) a number of meeting invitations initiated by the one or more sales representatives to the HCPs, or (5) a number of marketing communications sent by a company to the HCPs providing information on the pharmaceutical product.

In some embodiments, the inbound activity data may be collected over a plurality of communication channels comprising one or more of the following: (1) email communications; (2) mobile text messages; (3) social media websites; (4) mobile applications; (5) telephone calls; (6) in-person meetings; (7) video conferencing; (8) conferences or seminars; or (9) events conducted at the HCPs's facilities.

In some embodiments, the method may further comprise removing the effects of the inbound activity data from the adjusted sales data, and capturing residuals data from the predictive model after removing the effects of the inbound activity data.

In some embodiments, the data obtained from the plurality of data sources may further comprise (3) outbound activity data comprising a plurality of outbound features associated with actions taken by the plurality of HCPs.

In some embodiments, the plurality of outbound features may comprise (1) a number of visits by the HCPs to webpages associated with a company that is offering the pharmaceutical product for sale, (2) a number of communications between the HCPs and a sales representative for the pharmaceutical product, (3) a number of relevant symposiums attended by the HCPs, or (4) a number of endorsements by the HCPs of the pharmaceutical product.

In some embodiments, the plurality of outbound features may comprise the HCPs (a) opening one or more messages sent by the one or more sales representatives, (b) clicking on content or a hyperlink within the one or more messages, (c) replying to the one or more messages, (d) forwarding the one or more messages to one or more other parties, (e) deleting the one or more messages, (f) archiving the one or more messages, (g) posting or sharing the one or more messages on social media or a website, or (h) inaction or lack of action taken with respect to the one or more messages.

In some embodiments, the method may further comprise generating a plot of the residuals data as a function of the adjusted sales data, and determining a pattern in the plot, wherein the pattern is indicative of an association between the residuals data and one or more of the outbound features.

In some embodiments, the method may further comprise estimating effects of the outbound activity data on the adjusted sales of the pharmaceutical product to the plurality of HCPs, by using the residuals data as a second target in the predictive model.

In some embodiments, the method may further comprise ranking a plurality of outbound features based on the estimated effects of the outbound activity data, wherein the ranking is indicative of an importance or dominance of each of the plurality of outbound features.

In some embodiments, the method may further comprise generating an engagement model in which the estimated effects of the outbound activity data have been used to estimate the adjusted sales data, and using the engagement model to determine an engagement level of each of the plurality of HCPs with the one or more sales representatives.

In some embodiments, the engagement level may be provided as an engagement score.

In some embodiments, the method may further comprise identifying one or more optimal inbound activities by the one or more sales representatives to maximize the engagement score at any given time.

In some embodiments, the method may further comprise generating a chronological sequence of the one or more optimal inbound activities to maximize the engagement score over a time period.

In some embodiments, the method may further comprise generating a plot of the engagement score as a function of the residuals data, and determining a pattern in the plot. The pattern may be indicative of an association between the HCPs's engagement levels and the residuals data.

In some embodiments, the method may further comprise generating a plot of the engagement score as a function of the adjusted sales data, and determining a correlation coefficient from the plot. The correlation coefficient may be indicative of the HCPs's engagement levels contributing to the sales of the pharmaceutical product with the effects of the inbound activity data removed.

In some embodiments, the effects of the inbound activity data may be removed from the engagement model such that the engagement model is independent of inbound activity.

In some embodiments, the predictive model may utilize a machine learning algorithm. The machine learning algorithm may be selected from the group consisting of a random forest, a boosted decision tree, a classification tree, a regression tree, a bagging tree, a neural network, and a rotation forest.

According to another aspect, a system for estimating an impact of inbound activity on sales of a pharmaceutical product is provided. The system may comprise: a server in communication with a plurality of data sources; and a memory storing instructions that, when executed by the server, cause the server to perform a set of operations. The operations may comprise obtaining data from a plurality of data sources. The data may comprise (1) information associated with a plurality of healthcare providers (HCPs) and (2) inbound activity data associated with events or actions taken by one or more sales representatives relating to the sales of the pharmaceutical product. The operations may also comprise obtaining adjusted sales data by distributing aggregate sales values across the HCPs that are within each brick for a plurality of bricks associated with the plurality of HCPs, and estimating effects of the inbound activity data on the sales of the pharmaceutical product to the plurality of HCPs by using the adjusted sales data as a first target in a predictive model.

In a further aspect, a non-transitory computer-readable storage medium including instructions that, when executed by a server, cause the server to perform operations is provided. The operations may comprise obtaining data from a plurality of data sources. The data may comprise (1) information associated with a plurality of healthcare providers (HCPs) and (2) inbound activity data associated with events or actions taken by one or more sales representatives relating to the sales of the pharmaceutical product. The operations may also comprise obtaining adjusted sales data by distributing aggregate sales values across the HCPs that are within each brick for a plurality of bricks associated with the plurality of HCPs; and estimating effects of the inbound activity data on the sales of the pharmaceutical product to the plurality of HCPs by using the adjusted sales data as a first target in a predictive model.

In another aspect, a computer-implemented method for estimating an impact of outbound activity on sales of a pharmaceutical product is disclosed. The method may comprise obtaining data from a plurality of data sources. The data may comprise outbound activity data comprising a plurality of outbound features associated with actions taken by a plurality of healthcare providers (HCPs). The method may also comprise estimating effects of the outbound activity data on the sales of the pharmaceutical product to the plurality of HCPs by using residuals data from a predictive model. The residuals data may be obtained by removing estimated effects of inbound activity data from adjusted sales data in the predictive model. The adjusted sales data may be obtained by distributing aggregate sales values across the HCPs that are within each brick for a plurality of bricks associated with the plurality of HCPs.

In some embodiments, the plurality of outbound features may comprise (1) a number of visits by the HCPs to webpages associated with a company that is offering the pharmaceutical product for sale, (2) a number of communications between the HCPs and a sales representative for the pharmaceutical product, (3) a number of relevant symposiums attended by the HCPs, or (4) a number of endorsements by the HCPs of the pharmaceutical product.

In some embodiments, the plurality of outbound features may comprise the HCPs (a) opening one or more messages sent by the one or more sales representatives, (b) clicking on content or a hyperlink within the one or more messages, (c) replying to the one or more messages, (d) forwarding the one or more messages to one or more other parties, (e) deleting the one or more messages, (f) archiving the one or more messages, (g) posting or sharing the one or more messages on social media or a website, or (h) inaction or lack of action taken with respect to the one or more messages.

In some embodiments, the method may further comprise ranking a plurality of outbound features based on the estimated effects of the outbound activity data. The ranking may be indicative of an importance or dominance of each of the plurality of outbound features.

In some embodiments, the method may further comprise generating an engagement model in which the estimated effects of the inbound activity data has been removed from the adjusted sales data, and using the engagement model to determine an engagement level of each of the plurality of HCPs with the one or more sales representatives.

In some embodiments, the method may further comprise determining optimal sales and marketing strategies for each of the plurality of HCPs based in part on the engagement levels obtained from the engagement model.

According to another aspect, a system for estimating an impact of outbound activity on sales of a pharmaceutical product is provided. The system may comprise: a server in communication with a plurality of data sources; and a memory storing instructions that, when executed by the server, cause the server to perform a set of operations. The operations may comprise obtaining data from a plurality of data sources. The data may include outbound activity data comprising a plurality of outbound features associated with actions taken by a plurality of healthcare providers (HCPs). The operations may also comprise estimating effects of the outbound activity data on the sales of the pharmaceutical product to the plurality of HCPs by using residuals data from a predictive model. The residuals data may be obtained by removing estimated effects of inbound activity data from adjusted sales data in the predictive model. The adjusted sales data may be obtained by distributing aggregate sales values across the HCPs that are within each brick for a plurality of bricks associated with the plurality of HCPs.

In a further aspect, a non-transitory computer-readable storage medium including instructions that, when executed by a server, cause the server to perform operations is provided. The operations may comprise obtaining data from a plurality of data sources. The data may include outbound activity data comprising a plurality of outbound features associated with actions taken by a plurality of healthcare providers (HCPs). The operations may also comprise estimating effects of the outbound activity data on the sales of the pharmaceutical product to the plurality of HCPs by using residuals data from a predictive model. The residuals data may be obtained by removing estimated effects of inbound activity data from adjusted sales data in the predictive model. The adjusted sales data may be obtained by distributing aggregate sales values across the HCPs that are within each brick for a plurality of bricks associated with the plurality of HCPs.

It shall be understood that different aspects of the present disclosure can be appreciated individually, collectively, or in combination with each other. The embodiments described herein can be modified, combined and used in different configurations. Various aspects described herein may be applied to any of the particular applications set forth below. Other objects and features of the present disclosure will become apparent by a review of the specification, claims, and appended figures.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the present disclosure are set forth with particularity in the appended claims. A better understanding of the features and advantages of the present disclosure will be obtained by reference to the following detailed description that sets forth illustrative embodiments, and the accompanying drawings of which:

DETAILED DESCRIPTION

Figure 1:
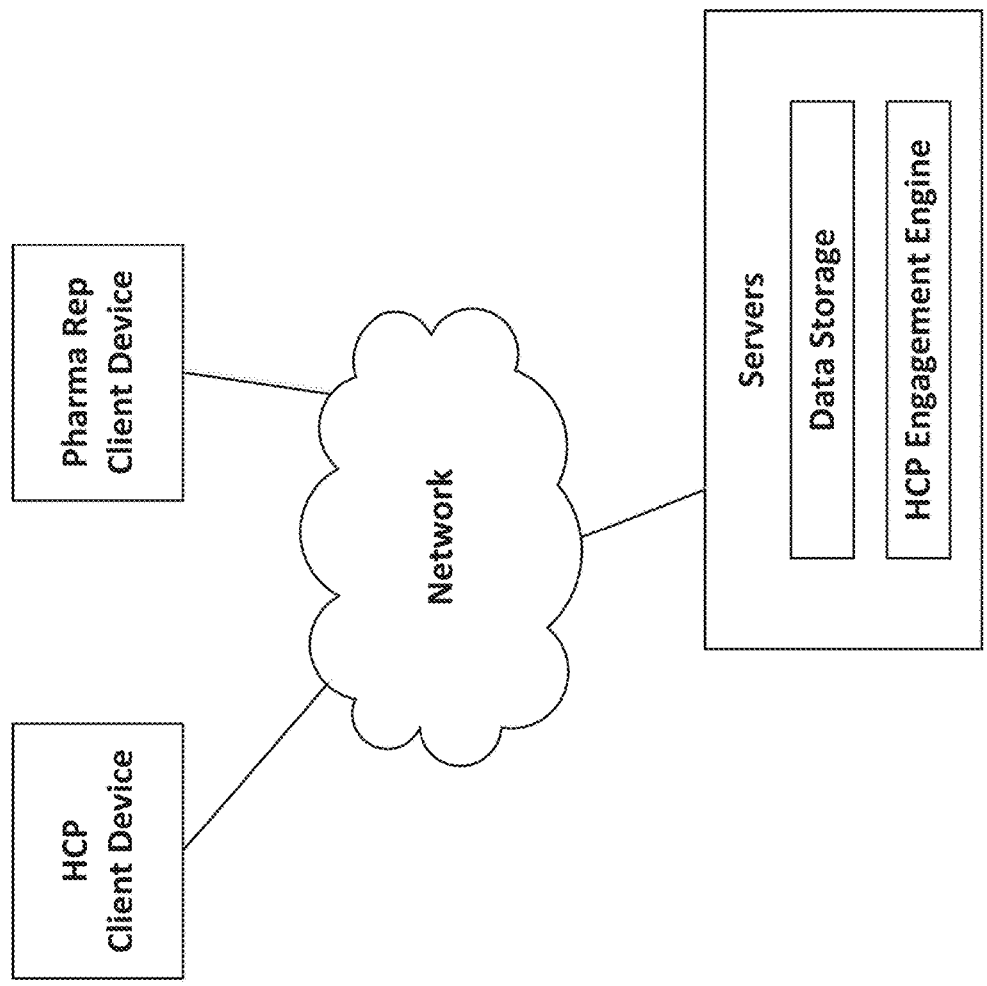
FIG. 1 shows a system comprising a health care provider (HCP) engagement engine in accordance with some embodiments.

The disclosed methods and systems can enable entities to improve and target their efforts in sales and marketing, by addressing at least the following challenges. For example, pharmaceutical sales representatives (pharma reps) who contact health care providers (HCPs) often need information about best practices for marketing treatments and medical services to the HCPs. Unfortunately, it is often difficult to assess which methods are most effective, given the limited data available and confounding effects that may occur during data collection processes.

First, interaction data between pharma reps and HCPs is often obscured. For privacy reasons, medical sales information may be unavailable, or may only be available at a facility level, or "brick" level. In a single brick, data from one or more HCPs may be aggregated. Thus, collecting brick-level data means that sales data for individual HCPs may not be obtainable, especially if bricks contain data from many different HCPs. In addition, data for some HCPs may be missing, inaccurate, or corrupted for some bricks. Data may also be obscured for privacy reasons. For example, hierarchy information may be missing from the sales-level data, if the HCP does not wish to make his or her identity known. HCP geographic information may also be obscured.

Second, sales data often may not reflect key interactions between pharma reps and HCPs. HCPs can wield strong influence on which pharmaceutical product/therapeutic to prescribe to patients, which can affect sales of a pharmaceutical product/therapeutic. For example, an HCP may have a good working relationship with one or more pharma reps, and if the HCP believes in the efficacy of the products and services that those reps are marketing, the HCP may be inclined to recommend prescribing products and services from those reps with whom the HCP has good working relationships. The HCP's recommendations on which products and services to prescribe to patients can significantly influence sales of those products and services. An HCP may also have a desire to experiment with new products, or may be personally susceptible to good salesmanship. The opposite may also be true—an HCP may be skeptical to try new products and services. HCPs may be inclined to prescribe products and services from pharma companies' offerings that they think would be effective in their medical practice, and may be less inclined to prescribe those products or services which they think are less effective. Some sales reps may be more experienced sellers, or have personal qualities which make them more effective at selling products or services. Some pharma companies may be widely regarded by HCPs and healthcare facilities, which may result in HCPs prescribing goods and services from those companies more often. Additionally, some companies may have exclusive business relationships with some HCPs or healthcare facilities. Products and services may be prescribed and thus purchased based on particular needs of providers, for example, if there is a particular disease or flu epidemic.

In order to mitigate the above effects or factors, they have to be first identified. The disclosed methods and systems can identify various factors that affect sales and that are not directly related to the pharma reps' sales efforts towards the HCPs. These factors can be separated into inbound effects and outbound effects, which may be derived from inbound activities and outbound activities, respectively. In addition, attributes of the HCPs, referred to herein as covariates, may also affect the sales analysis.

Some examples of inbound activities may include visits from pharma reps to doctors, messages (such as e-mail messages) sent to HCPs from pharma reps, phone calls from HCPs or HCP employees to pharma reps, and web details, such as webinars or web-based conferences. Inbound activities are not limited to activities directed by the external entity to the individual HCPs. In some instances, inbound activities may include any relevant activities undertaken by one or more pharma reps at the direction of the external entity to the individual HCPs. The inbound activities may be organized into a matrix form.

Some examples of outbound activities may include time elapsed between a HCP's receipt and opening of an email from a pharma rep, a visit by the HCP to the pharma rep's webpage or another relevant webpage, or the HCP attending a conference related to the pharma rep's field. Outbound activities may be include any relevant activities undertaken by the HCPs, or one or more persons at the direction of the HCPs, that are directed towards one or more pharma reps or to an entity that provides direction to the pharma reps. Similar to the inbound activities discussed above, these outbound activities may also be organized into a matrix form.

Covariates may include, but are not limited to, a facility at which an HCP works or is assigned (e.g., a hospital, medical office, etc.), a segment or specialty (e.g., cardiology, radiology, etc.), or an associated brick (e.g., associated facility, group, collection of facilities, etc.).

In some embodiments, the method disclosed herein may proceed first by disaggregating per-brick sales data to form adjusted sales data, and then de-confounding effects from the inbound and outbound activities. Disaggregating the data, in this context, may include distributing the total sales per brick among all of the HCPs within the bricks. The disaggregation may include assumptions that HCPs who are more engaged, and who typically generate larger amounts of outbound activity, are responsible for a relatively larger proportion of sales. Adjusting sales may thus include distributing the sales per brick among the HCPs within that brick with respect to the outbound activities of the HCPs.

Next, the method may include correcting for the effects from inbound activities. The effects from inbound activities may be corrected by fitting a function which takes as arguments values of inbound activities and covariates, and returns the adjusted sales calculated from the previous step. Following this step, the method may next calculate a set of residuals, in order to determine additional confounding effects that may be present in the data. Next, the method may correct for outbound activity by fitting a function taking as arguments the outbound effects and returning the set of residuals from the inbound correction step. This is performed to correct for any effects caused by the outbound effects.

The model fitting may be performed by linear or nonlinear methods. Linear methods may include linear regressions. Nonlinear methods may include decision tree algorithms, such as gradient tree boosting, bagging, or random forest algorithms.

FIG. 1 shows a system 100 comprising a health care provider (HCP) engagement engine. The system may include a network, one or more client devices, and one or more servers.

The network may be a computer network such as a local area network (LAN), a wide area network (WAN), a wireless local area network (WLAN), a metropolitan area network (MAN), a storage area network (SAN), a campus area network (CAN), or a personal area network (PAN). The network may be a wired or wireless network, such as a Wi-Fi network. The network may include servers, routers, switches, and other network devices and services to facilitate transfer of data, including session data, control data, commands and other communication between the various parts of the system.

The client devices may be computing devices. For example, they may include mobile computing devices, such as cellular phones, smartphones, personal assistants, and tablet computers. They may also include laptop computers, terminals, or desktop computers. The client devices can allow for information exchange between different parties, namely, the pharma reps and the HCPs. One or more of the client devices may be associated with one or more pharma reps ("Pharma Rep Client Device"). One or more client devices may be associated with one or more health care providers (HCPs) ("HCP Client Device"). The health care providers may include physicians, nurses, nurse practitioners, pharmacists, scientists, researchers, or technicians. Pharma reps and HCPs may communicate using their client devices, for example using methods of text-based online or networked communication such as email, instant messaging, internet chat protocols, message boards, or bulletin board systems (BBS). Messages may also include mobile text messages as well as messages from social media websites, mobile applications, telephone calls, in-person meetings, video conferencing, conferences or seminars, or associated with events conducted at an HCP's work facility.

The pharma rep client devices may transmit information to the servers, including actions taken by pharma reps, for analysis. The pharma rep client devices may receive recommendations, such as recommended messages or suggested methods to contact HCPs, from the servers, and present them to the pharma reps. The pharma rep client devices may have software installed that provides a user interface (UI) for presenting such recommendations. The software may integrate with applications that enable networked communication, such as customer relations management (CRM) systems including Veeva CRM and IQVIA CRM, as well as other software applications including MICROSOFT® OUTLOOK, GOOGLE® HANGOUTS, APPLE® iCHAT, and FACEBOOK® MESSENGER. For example, the software may extend the chat applications to provide popup notifications or additional windows in which information is presented to the pharma reps. The pharma rep client devices may periodically retrieve recommended messages from the servers, or may retrieve messages when a pharma rep submits a request for a recommended message to be provided from the servers. The HCP client devices may also have networked communications programs installed on them, and may present messages sent by the pharma reps to the HCPs. Both the pharma rep client devices and the HCP client devices may have software installed on them that can log actions taken respectively by the pharma reps and the HCPs, and send records of these actions to the servers. The actions logged may include mouse clicks, keystrokes, or interactions with onscreen elements. The actions may be sent to the servers along with timestamps, in order for the servers to record them as time-binned data for machine learning analysis.

The servers may be physical servers or virtual servers. Physical servers may be deployed in a server farm environment. Virtual servers may exist in a cloud computing environment or a distributed computing environment. The servers may store data and perform data analysis. The servers may include one or more data storage systems. The data stores may contain message data, pharmaceutical representative (pharma rep) data, and HCP data. The pharma rep data may include drugs and treatments sold by the pharmaceutical representatives. The HCP data may include the specialties or practice areas of the HCPs, the hospitals or institutions to which they are affiliated, and the seniority levels of the HCPs. Pharma rep and HCP data may also include demographic information, such as age, education, location, and ethnicity. The data stores may also store electronic representations of the pharma market strategies, e.g. preferred or optimal timing of pharma reps' visits and message sends to HCPs, specific instructions for targeting segments of HCPs, guidelines for targeting and improve engagement with HCPs, sequence and types of inbound activities, etc.

The servers may receive data from the client devices, including the pharma rep client devices and the HCP client devices. The servers may communicate through the network with computer programs installed on the client devices, in order to request data from the client devices in order to perform machine learning analysis. For example, the servers may periodically make requests for action data. The servers may request data on a monthly, weekly, or daily basis, or at predetermined time intervals. In some embodiments, the client devices may be able to opt in or opt out of sharing particular data items or categories of data with the servers. The servers may have installed one or more computer programs to aggregate and organize the data. One of the computer programs may be configured to determine if data sampled from one or more of the client devices is deficient, and may request additional data from the client devices if necessary.

The HCP engagement engine can be configured to evaluate the effectiveness of pharma rep actions towards HCPs on sales. The HCP engagement engine may analyze data from the data stores within the servers in order to produce an engagement score. The HCP engagement score may be dependent on HCP engagement only, and may be independent of HCP attributes and inbound activity. In order to produce the engagement score, the HCP engagement engine may first remove confounding effects caused by some of the data. Data that may cause confounding effects may include inbound activity data, outbound activity data, and attributes of the HCPs and pharma reps. When these confounding effects are removed, the HCP engagement engine may then assess HCP engagement as a function of pharma rep actions. The HCP engagement engine may use one or more machine learning algorithms or statistical methods to perform this analysis. The HCP engagement engine may use a random forest model to predict an HCP action following one or more pharma rep actions. For example, the HCP engagement engine may be used to predict whether an HCP will open a message sent by a pharma rep, given that the pharma rep sent it within a sequence of other messages, at a specific time, and that the message contained specific content.

In some embodiments, the HCP engine may create a score from a set of actions, or a set of action sequences. It then may select an action, or sequence of actions, with a maximum score. This may be represented by equation (1):

$$i^* = \mathrm{argmax}_i(\mathrm{HES})$$

In the above equation, $i^*$ represents a selected action, which is the action that produces the largest HCP engagement score (HES). This expression may be time-dependent, with the scores of actions changing based on time. A similar expression may be used to determine a sequence of actions with a maximum HES among a set of sequences of actions.

The system may provide insights or recommendations as to which action or sequence of actions would be preferred, based on the calculated HES. These insights or recommendations may be provided to pharma reps on their client devices, for example, using a mobile application with a graphical user interface. They may also be provided to the pharma reps using a method of networked communication, such as email communication.

Figure 2:
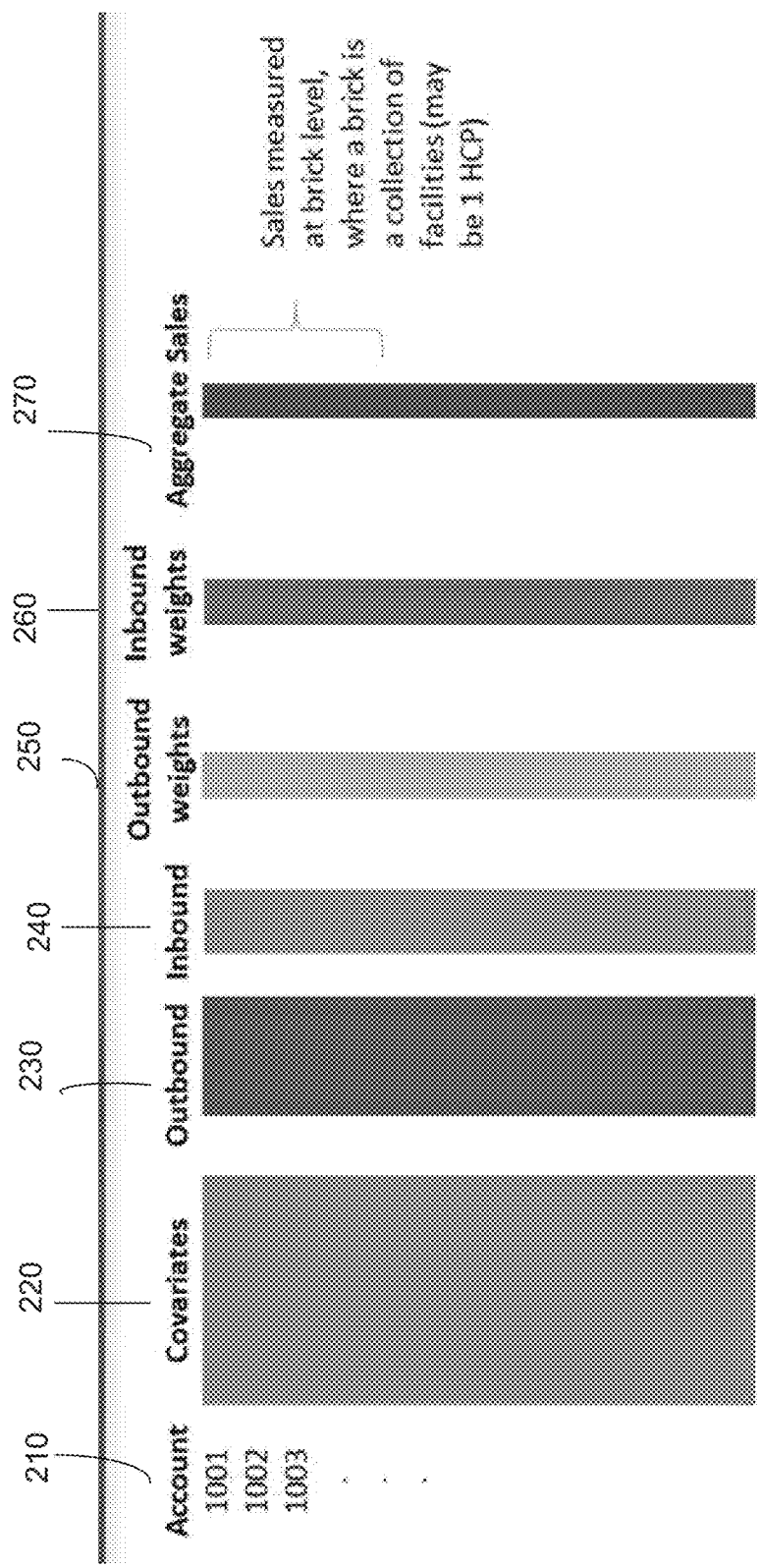
FIG. 2 shows examples of data types that can be analyzed by the system in order to account for inbound and outbound activities, in accordance with some embodiments.

FIG. 2 is an illustration of the data types that can be analyzed by the system in order to account for inbound activities and outbound activities. The data types may include account information 210, covariates 220, inbound data 240, outbound data 230, outbound weights 250, and inbound weights 260. Data within the above data types may include quantitative and/or qualitative data. The data may be in matrix or vector form, and may include binary, continuous, or category-type data.

The data may be imported into the system from many different data sources. Data sources may include customer relationship management (CRM) systems, pharmaceutical proprietary databases, market segmentation, and sales data. Data from these disparate sources may be processed by the system, in order to produce standardized data with specific fields that may be used by the algorithms disclosed herein for analysis. Data for a particular account may be provided by one or more data sources, and different data fields from these data sources may be consolidated into one data entry for a particular account.

The account information 210 may include an individual account managed by a pharma rep. An account may correspond to an individual HCP, or an individual facility comprising of one or more HCPs. Individual bricks of data may include data from one or more accounts. The accounts may be assigned number labels (e.g. 1001, 1002, 10003 and so forth) or name labels. The accounts may be related to one or more bricks, depending whether the accounts relate to individuals or facilities. In some situations, HCPs may be affiliated with multiple facilities, and thus an account may be related to multiple bricks simultaneously. Account information may be updated when a new HCP is registered with a facility, or when HCPs move to different facilities or are no longer active.

Covariates 220 include various attributes of HCPs. Covariates 220 may include demographic information, such as specialty, facility, years of experience, occupation, purchasing habits, age, title, and information concerning the relationship between the HCP and the pharma rep. The covariates 220 may be correlated with one another, correlated with one or more of the inbound variables, correlated with one or more of the outbound variables, or independent of one another and of any of the variables. For example, HCPs who are older may have more seniority and more years of experience. Older HCPs may have better personal relationships with specific pharma reps, as they may have had more contact with the reps. The covariates 220 may be continuous, categorical, or binary variables. Binary variables may include whether an HCP has displayed interest in a drug/therapeutic, made a recommendation to a facility or to coworkers, and/or wrote a prescription for the drug/therapeutic to patients in a particular timeframe, such as during a particular day, week, month or year. Binary variables may also include whether an HCP has performed an action on a communication from a pharma rep. Continuous variables may include time-binned patient volume, tracked volumes of communications sent and received, time spent performing various patient care-related activities, and cumulative drug and therapy prescriptions. Categorical variables may include specialty, seniority, years of experience, attending facility, education, marital status, conferences attended, ethnicity, and working hours.

Outbound activities 230, or variables, may be actions taken by HCPs in response to actions performed by pharma reps, that relate directly or indirectly to the actions performed by the pharma reps. The outbound activities 230 may include (1) a number of visits by the HCPs to webpages of a company that is offering the pharmaceutical product for sale, (2) a number of communications from the HCPs to one or more sales representatives for the pharmaceutical product, (3) a number of relevant symposiums attended by the HCPs, or (4) a number of endorsements by the HCPs of the pharmaceutical product. Outbound activities 230 may yield outbound features, which may be entered into the system as data and used for analysis. The outbound features may be analyzed in order to determine what effects the features have on HCP engagement level. The outbound features may be related to one another, independent, related to the inbound features, or related to the covariates. In some cases, the plurality of outbound features may comprise the HCPs (a) opening one or more messages sent by the one or more sales representatives, (b) clicking on content or a hyperlink within the one or more messages, (c) replying to the one or more messages, (d) forwarding the one or more messages to one or more other parties, (e) deleting the one or more messages, (f) archiving the one or more messages, (g) posting or sharing the one or more messages on social media or a website, or (h) inaction or lack of action taken with respect to the one or more messages.

Inbound activities 240, or variables, may be actions performed by pharma reps and/or pharma companies towards HCPs, for the purpose of marketing and selling products or services to the HCPs. In addition to the pharma reps' efforts, pharma companies may send communications directly to HCPs which may be in the form of marketing materials (electronically or in paper), advertisements on various media or channels, invitations to attend seminars, etc. The inbound activities (or variables) may be independent or functions of one another or of the covariates. In some instances, they may have some correlation with the outbound variables. Inbound activities may be catalogued to create inbound features, which may be analyzed for the system in order to determine HCP engagement. In some cases, a plurality of inbound features in the inbound activity data may comprise (1) a number of visits by the one or more sales representatives to the HCPs, (2) a number of electronic communications sent by the one or more sales representatives to the HCPs, (3) a number of telephone calls from the one or more sales representatives to the HCPs, (4) a number of meeting invitations initiated by the one or more sales representatives to the HCPs, or (5) a number of marketing communications sent by a company to the HCPs providing information on the pharmaceutical product. The inbound activities 240 may be collected over one or more communication channels comprising one or more of the following: (1) email communications; (2) mobile text messages; (3) social media websites; (4) mobile applications; (5) telephone calls; (6) in-person meetings; (7) video conferencing; (8) conferences or seminars; or (9) events conducted at the HCPs' facilities.

In order for the system to perform analysis on the outbound features and inbound features, the outbound and inbound features may be represented in matrix form. For example, the rows in the inbound feature matrix may be individual account numbers or labels, which may represent HCPs or bricks. The columns may be inbound features, with each column representing a specific category. Thus, a specific row-by-column 2D index may represent a particular feature value from a particular account. If feature data for a specific index is unavailable, it may be interpolated from other feature values.

In some embodiments, the inbound features and outbound features may have inbound weights 260 and outbound weights 250 applied to them. These weights may be scalar numbers within a vector that can be applied to the outbound features in order to improve accuracy of the analysis. The weights may be applied using one or more vector multiplication operations. These weights may be described and input by an end user, or may be generated using a machine learning algorithm or statistical method. Larger weights may be applied to features that have higher value or more importance in confounding, where smaller weights may be applied to features that have lower value or less importance in confounding. The weights may be configured to change in response to conditions. For example, particular actions may have more or less significance depending on the time of day, week, or month in which they occur. Additionally, as more data is retrieved by the system, the system may learn information about inbound and outbound actions that may lead clients to reassess the importance of one or more of these actions. The weights can be configured to capture the "opinions" of the pharma marketing departments on the importance of the various outbound and inbound factors. As an example, a HCP's attendance at a webinar may be weighted twice as important as a HCP's visit to a web site in terms of the value of the outbound interactions. Although FIG. 2 schematically illustrates the weight as columns in the matrix, it should be understood that the weights are actually vectors that multiply the rows of the matrix—i.e. each column gets weighted.

Aggregate sales 270 may be organized by bricks. Bricks may include data collected from facilities. A brick may include one or more facilities, which in turn may have one or more HCPs. An individual brick may contain facilities that have in common one or more factors including geographical region, location, size, number of HCPs, socioeconomics of a region, or demographics of a region. Bricks used in the analysis may or may not be of uniform size. Some of the bricks used in the analysis may come from facilities containing one HCP, and other bricks may come from facilities having multiple HCPs.

The adjusted sales data may comprise sales values disaggregated at an individual level instead of at a brick level. In some embodiment, disaggregation may be performed by determining average sales per HCP within a brick (by dividing the total sales in the brick by the number of HCPs contained in the brick). Next, the system may determine adjusted sales per HCP. The system may assume that highly engaged HCPs are more likely to have prescribed or recommended certain pharma products or services for prescription to patients. Thus, HCPs that are more engaged are allotted higher proportions of adjusted sales, while HCPs that are less engaged are allotted lower proportions of adjusted sales.

Figure 3:
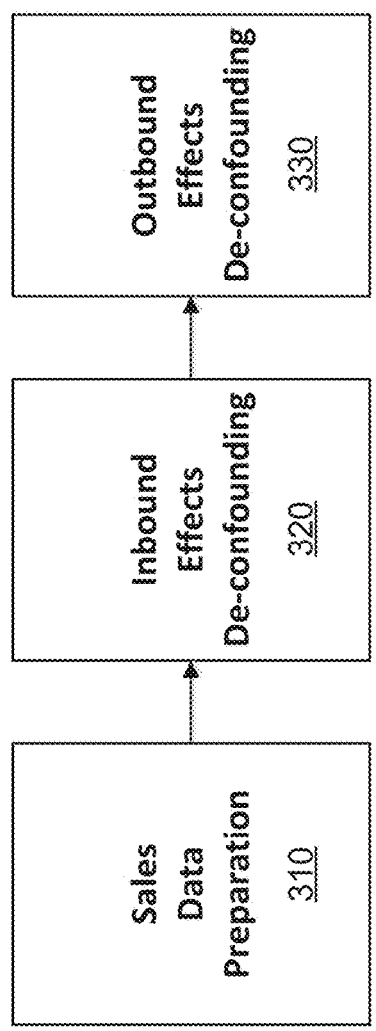
FIG. 3 is a block diagram illustrating different functions of the system in accordance with some embodiments.

FIG. 3 is a block diagram illustrating different functions of the system in accordance with some embodiments. The block diagram of FIG. 3 shows sales data preparation/adjustment 310, de-confounding inbound activity effects 320, and de-confounding outbound activity effects 330. The term "de-confounding" can mean "unconfounding," and the terms may be used interchangeably herein. The steps of de-confounding inbound activity effects and de-confounding outbound activity effects may be performed interchangeably. As disclosed herein, sales data adjustment may be performed with respect to outbound activity. In various embodiments, sales data adjustment may be performed using other types of collected data.

Sales data preparation 310 may include distributing brick-level sales data across HCPs within the brick. Data may be obtained from multiple sources, and the distribution of sales data may be performed across all of the HCPs within a brick. Unlike individual sales data, HCP engagement may be directly measured, by logging activity data from HCPs in the servers. HCPs with high outbound activity may be assumed to be exhibiting high engagement, and thus likely may account for a larger percentage of sales than those with lower outbound activity, which provides the premise of the sales distribution approach. Adjusting sales data may include applying weights to the average sales per-brick, or unadjusted sales, based on HCP outbound activity for HCPs within the bricks. This may be performed by using a matrix multiplication method to project the unadjusted sales data onto a space formed by the outbound activity data. The adjusted sales data can be used as a target in a predictive model, such as the HES model described herein, to estimate impacts of different marketing strategies on the sales of the pharmaceutical product. Other predictive models may also be developed to estimate impacts of marketing strategies that also leverage adjusted sales data, and to account for confounding using different methods as described herein.

In some cases, pharma companies may classify the outbound features such that some features are weighted more than others. This weighting may also be performed by matrix multiplying the outbound features with a matrix or vector of outbound weights. Following the inbound processing stage, the system may calculate residuals, by applying the fitted function to available sets of inbound features and measuring the deviation in adjusted sales from what is predicted by the function. From these residuals, the system may then perform processing on the outbound activity data.

Distributing within brick sales to HCPs may be performed using a simple linear model or by a non-linear model. In some embodiments, distributing within brick sales to HCPs may involve using a pseudoinverse as described elsewhere, which may be preferable for the simplicity of the linear model. Linear models may include linear regressions. Non-linear models may include decision tree-based models, such as gradient boosted trees, classification trees, regression trees, bagging trees, and random forests. They may also include neural network-based models.

An implementation of the sales adjustment process is described as follows. In one example, the unadjusted overall sales data may be distributed across providers in brick b by first solving equation (2) for x.

$$o_b x = s_b \qquad \text{Equation (2):}$$

In Equation (2), submatrix $o_b$ identifies the outbound activities of the providers associated with the brick b and subvector (e.g., column vector), and $s_b$ identifies sales (or prescribing) activity of the providers associated with the brick b.

To determine the distributed sales data per provider adjusted to (or based on) each provider's outbound activities, Equations (3) and (4) may be solved.

$$x^* = o_b^+ s_b \qquad \text{Equation (3):}$$

$$o_b x^* = \bar{s}_b \qquad \text{Equation (4):}$$

In Equation (3), $o_b^+$ is the psuedoinverse of $o_b$, and the projection $\bar{s}_b$ of Equation (4) provides the sales adjusted to the providers' outbound activities (also referred to as the "outbound activity distributed sales values").

The solution $o_b x^*$ of Equation (4) provides the distributed sales data per provider (also referred to as the "adjusted sales values").

In an embodiment in which the outbound activities are given different weights, a weighted outbound activities matrix $o_b^w$ may be provided by solving Equation (5).

$$o_b^w = o_b I w_o \qquad \text{Equation (5):}$$

In Equation (5), I is an identity submatrix and $w_o$ is an outbound activity weights submatrix. After Equation (5) is solved for $o_b^w$, the weighted outbound activity submatrix may be used in place of $o_b$ in Equations (2)-(4) to provide weighted outbound activity distributed sales values.

In another example, a number of providers (e.g. three) may be assigned to (e.g., practice in) a particular brick b. In this example, the first provider has attended two symposiums during the relevant time period, the second provider has visited a relevant website once during the relevant time period, and the third provider has attended one symposium during the relevant time period. Thus, the first provider has a higher engagement level than either the second provider or the third provider. The providers' outbound activities provide the following outbound submatrix $o_b$, in which the rows indicate the three providers and the columns indicate the different outbound activities with website visits in the left column and symposium attendance in the right column.

$$o_b = \begin{pmatrix} 0 & 2 \\ 1 & 0 \\ 0 & 1 \end{pmatrix}$$

In this example, the obscured overall brick sales (e.g., the sum of all sales in a particular brick) may be three, and thus, the average brick-level sales per provider is equal to one during the relevant time period, which provides the following subvector $s_b$ $$s_b = \begin{pmatrix} 1 \\ 1 \\ 1 \end{pmatrix}$$

The pseudoinverse of $o_b$ is as follows.

$$o_b^+ = \begin{pmatrix} 0.0 & 1 & 0 \\ 0.4 & 0 & 0.2 \end{pmatrix}$$

The sales adjusted to the providers' outbound activities (also referred to as the "outbound activity distributed sales") is provided as follows:

$$\overline{s_b} \equiv T_b(o)s_b = o_b o_b^+ s_b = \begin{pmatrix} 1.2 \\ 1.0 \\ 0.6 \end{pmatrix}$$

wherein $T_b(o)=o_b o_b^+$.

As is seen in the above matrix $\overline{s_b}$, the first provider is considered to have the greatest relative share of sales among the three providers in the particular brick b since the first provider had two outbound activities (i.e., two symposium visits) while the second and third providers had only one outbound activity each (i.e., one website visit and one symposium visit, respectively).

The above is an example of a linear model in which the pseudoinverse is used. As previously noted, an advantage of the model is that it is simple to use. Nonetheless, it should be noted that non-linear models which are more complex may be used in some other embodiments.

The inbound de-confounding stage 320 can account for the effects of inbound activities on HCP engagement. In order to achieve this, the system may fit a function of inbound features and covariates to the adjusted sales. This may be performed using a nonlinear method, such as with a random forest algorithm. When the random forests algorithm has been performed, the system may determine relative importances for the covariates and inbound activities, in order to determine which had contributed most to adjusted sales.

In one embodiment, the impact of the inbound activities is reduced by fitting a function f(c, i). For example, a model f(c, i)=s* is fit where s* is a vector of per-brick adjusted sales:

$$s^* = \begin{pmatrix} s_{b_1}^* \\ s_{b_2}^* \\ \vdots \end{pmatrix}$$

The model f(c, i) includes the attributes (e.g., the matrix of attributes or covariates) because the inbound activities may be highly related or correlated with the particular provider attributes. For example, younger providers may be more receptive to e-mails rather than phone calls, and it may be found that providers with an age attribute of under than "35," for example, may be exposed to a greater number of phone call inbound activities.

In some embodiments, weights may be applied to the inbound features. In this embodiment, instead of fitting f(c, i)=s*, the weighted inbound activities submatrix $i_w=iIw_i$ is used.

Finally, the system can account for outbound effects during the outbound effects processing stage. The system can again fit a model, this time to the residuals calculated from the step of de-confounding the inbound effects. The model can fit the outbound effects to the residuals in order to account for the outbound activity effects.

During the outbound de-confounding stage 330, the remaining effects relevant to the sales data are attributed to each provider's outbound activities by modeling h(o)=s*. The resultant model h*(o) provides a correlation between the obscured overall sales data, the outbound and inbound activities collected during the inbound activity processing stage, and estimated sales per provider in a particular brick based on each provider's outbound activities relatively irrespective of the inbound activities. The resultant correlation provides an indication of how "engaged" a particular provider is with a company (e.g., a pharmaceutical company) irrelevant of the inbound activities, which are the actions performed by that company to the providers. By using this information, the company can determine which of the providers in a particular brick are prescribing a relevant product (e.g., a pharmaceutical drug) irrespective of the company's marketing efforts, thus allowing the company to better utilize its limited marketing resources by targeting the providers modeled to be somewhat engaged and likely to become more engaged over time.

The outbound features may be ranked in order to determine which features correlate most strongly with HCP engagement. Generating a ranked list showing relative importances of outbound features may enable pharma companies to determine which outbound activities from HCPs to monitor, in order to determine which HCPs are most strongly engaged and, thus, likely to procure products and services from pharma reps. This data can allow pharma companies to determine optimal sales and marketing strategies for each of the plurality of HCPs based in part on the engagement levels obtained from the engagement model.

Figure 4:
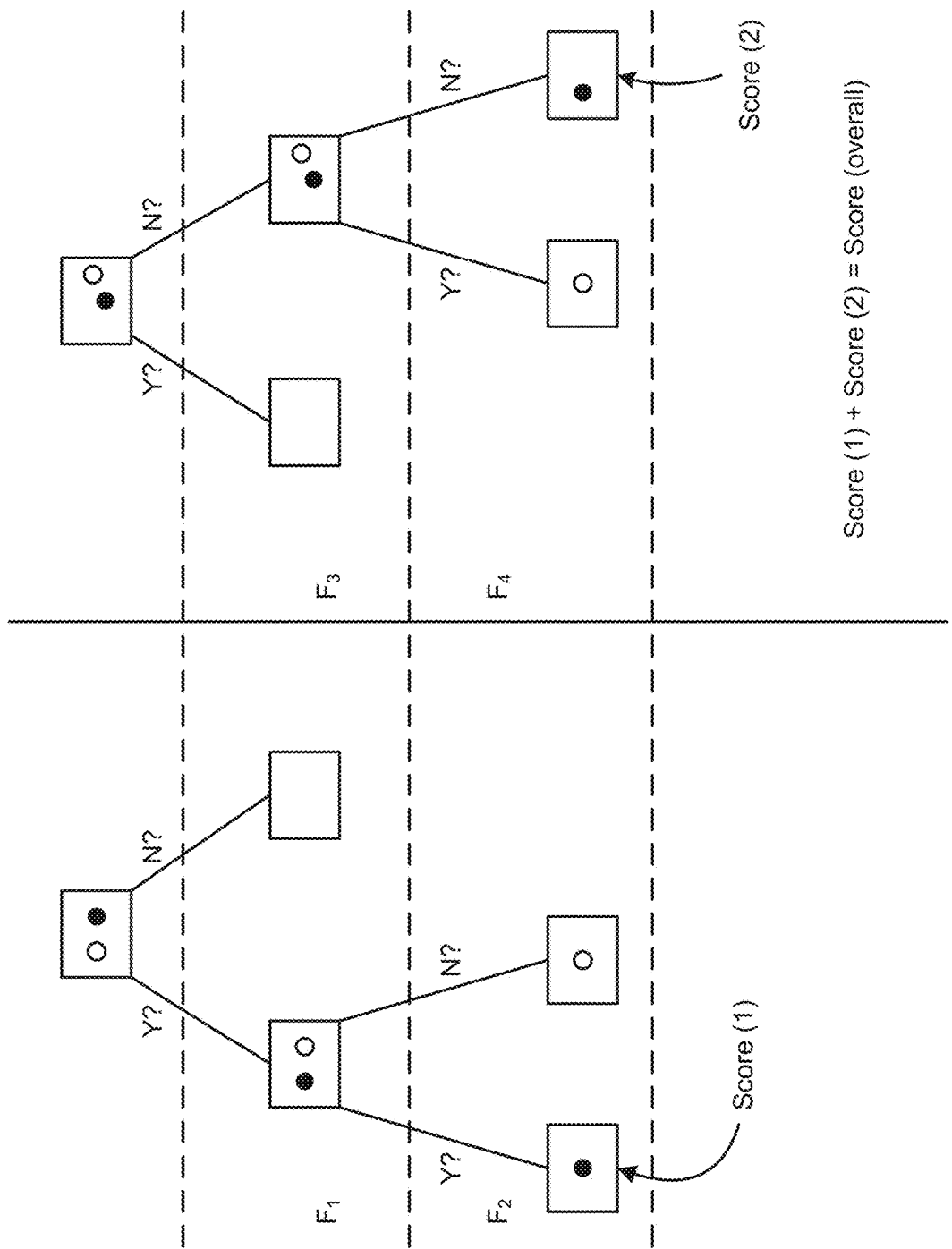
FIG. 4 shows a random forest algorithm in accordance with some embodiments.

FIG. 4 shows a random forest algorithm that can be used with embodiments of the present disclosure. Random forests are an ensemble learning method for classification, regression and other tasks that operates by constructing a multitude of decision trees at training time and outputting the class that is the mode of the classes (classification) or mean prediction (regression) of the individual trees. Random decision forests can correct for decision trees' habit of overfitting to their training set.

Using a single tree to classify a large data set is often not desirable. Decision trees classify elements within a data set by iteratively partitioning the data set with respect to individual characteristics of the elements of the data set. These characteristics are called features. In order to properly classify data elements, partitions may need to only contain a few elements each. In a decision tree, a partition is made by comparing elements using a threshold for a feature. For example, a population may be split into two groups, with one group having brown eyes and the other group not having brown eyes. This split may be visualized as a branch, with the elements at the bottom of each branch visualized as leaves or nodes. For large data sets, many partitions need to be made. When training a decision tree, creating too many partitions may result in a low-bias, but high-variance, data set. Thus, creating too many partitions using a single deep decision tree may result in overfitting.

In order to avoid overfitting when classifying data using decision trees, several machine learning algorithms have been developed. One of these methods is the random forest method. The random forest method creates many trees and averages them, reducing the variance and boosting performance. For each created tree, a random forest algorithm selects a random subset of features. This process is called bootstrap aggregating, or bagging. The number of trees to be created may be set by a developer, and may be in the hundreds. An individual decision tree may be grown to a particular length, or number of branching decisions. For example, the number of features used may be set by a developer. Alternatively, the length of the tree may be determined based on a convergence condition, such as a minimization of a loss function. Once all of the trees have been implemented, the classification results from the trees are aggregated. For example, each classification group (node or leaf) at the bottom of each tree may be given a score, and these scores may be added together to produce a total classification score for each classification group. All of the elements in each group have the same score. These scores may be mapped to qualitative values. In the preceding example, the random forest method may give all of the subjects with brown eyes scores greater than 0.5, and all the subjects without brown eyes scores less than 0.5.

FIG. 4 shows a simple example of a random forest with two decision trees. Each decision tree has two splits, based on a different "random" set of two features. The left tree splits on features 1 and 2, while the right tree splits on features 3 and 4. Each tree analyzes a set of elements, which includes the feature of interest, designated by a black, filled-in circle. Although each tree analyzes the same number of elements, the remaining elements, designated by unfilled, white circles, are not necessarily the same. This is because, in this implementation, each tree randomly selects a fixed-size subset of elements for analysis. Each level of the tree corresponds to a binary decision. In FIG. 4, the decision is a yes or no decision. At each level of the tree, elements are classified on the basis of the binary decision with respect to the feature at each level. The terminal nodes, or leaves, represent the final classifications of the elements. Based on these classifications, the elements are given scores. On the left tree, the black, filled-in circle is given score (1). On the right tree, the black, filled-in circle is given score (2). These scores are added to produce an overall score for the black, filled-in circle element. The white, unfilled circles also receive scores, although they are not shown in the figure.

Although random forest algorithms are described here, other methods that aggregate scores from decision trees in order to classify data elements may also be used. These methods include gradient boosted trees, other types of bagged trees, rotation forests, and decision lists.

Figure 5:
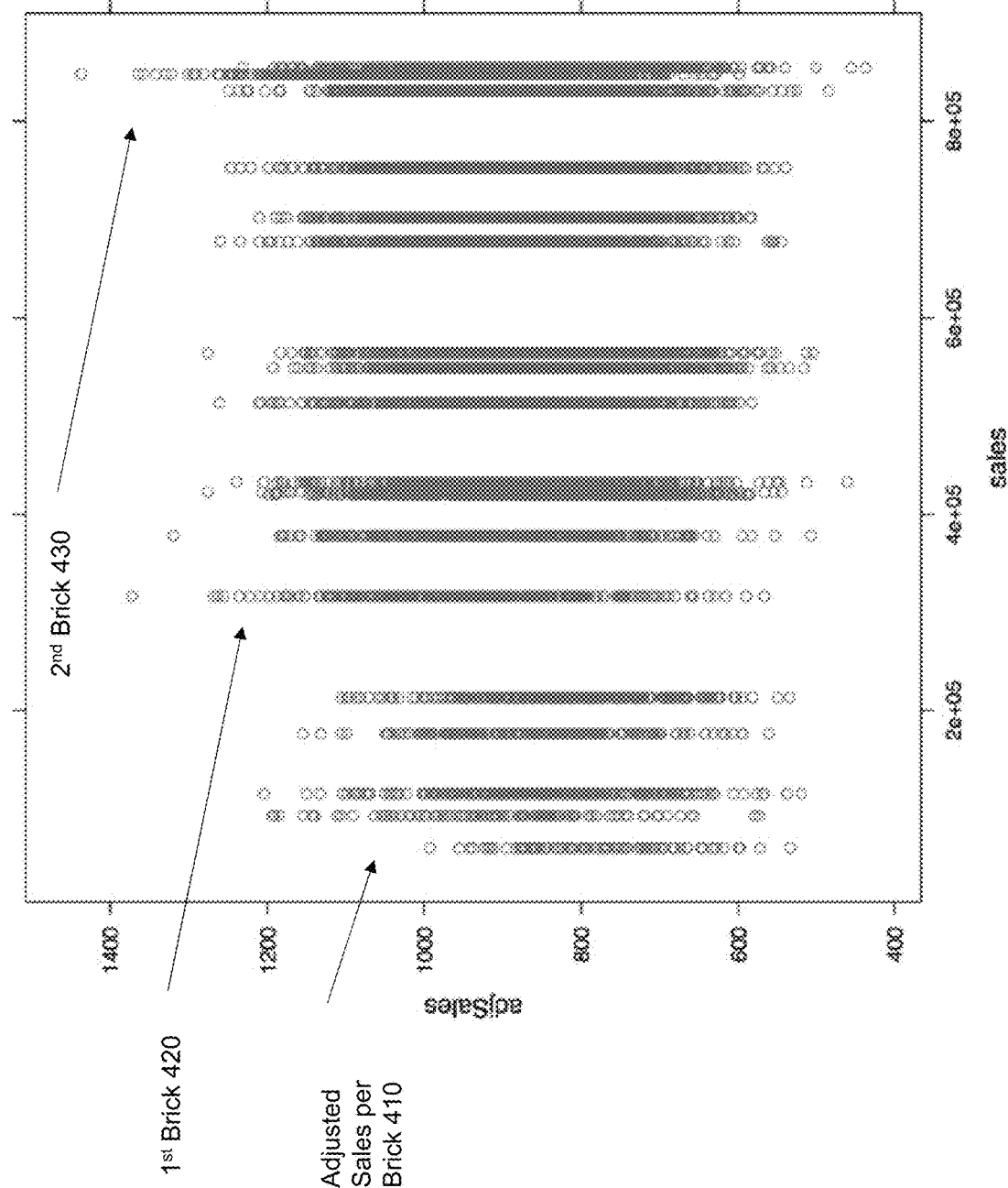
FIG. 5 shows an illustration of the impact of outbound features projected onto the sales by HCP, in accordance with some embodiments.

FIG. 5 shows an illustration of the impact of the outbound features was projected onto the sales by HCP, in accordance with some embodiments. The plot shows data adjustment for "synthetic" data created from a simulation designed to capture the mean and covariance behaviors one might see in practice. The plot shows adjusted sales versus sales from this data which had 10,000 observations of HCPs, four outbound variables, and ten bricks. Illustrated are, for average brick sales, adjusted sales 410 for all of the HCPs in the analysis. For a particular average sale value, there are a range of estimated sales for the HCPs. Wider bands may have more variation in average sales, or may also be wider because more HCPs are contained in the underlying bricks.

The plot shows adjusted sales for 17 bricks. The bricks may represent one or more accounts. In FIG. 5, all of the bricks contain sales data for multiple accounts. The plot shows a first brick 420 showing a range of adjusted sales in one brick, with total sales of about 400,000. The plot also shows a second brick 430, with total sales of about 650,000, with a range of adjusted sales for the HCPs within that brick.

Figure 6:
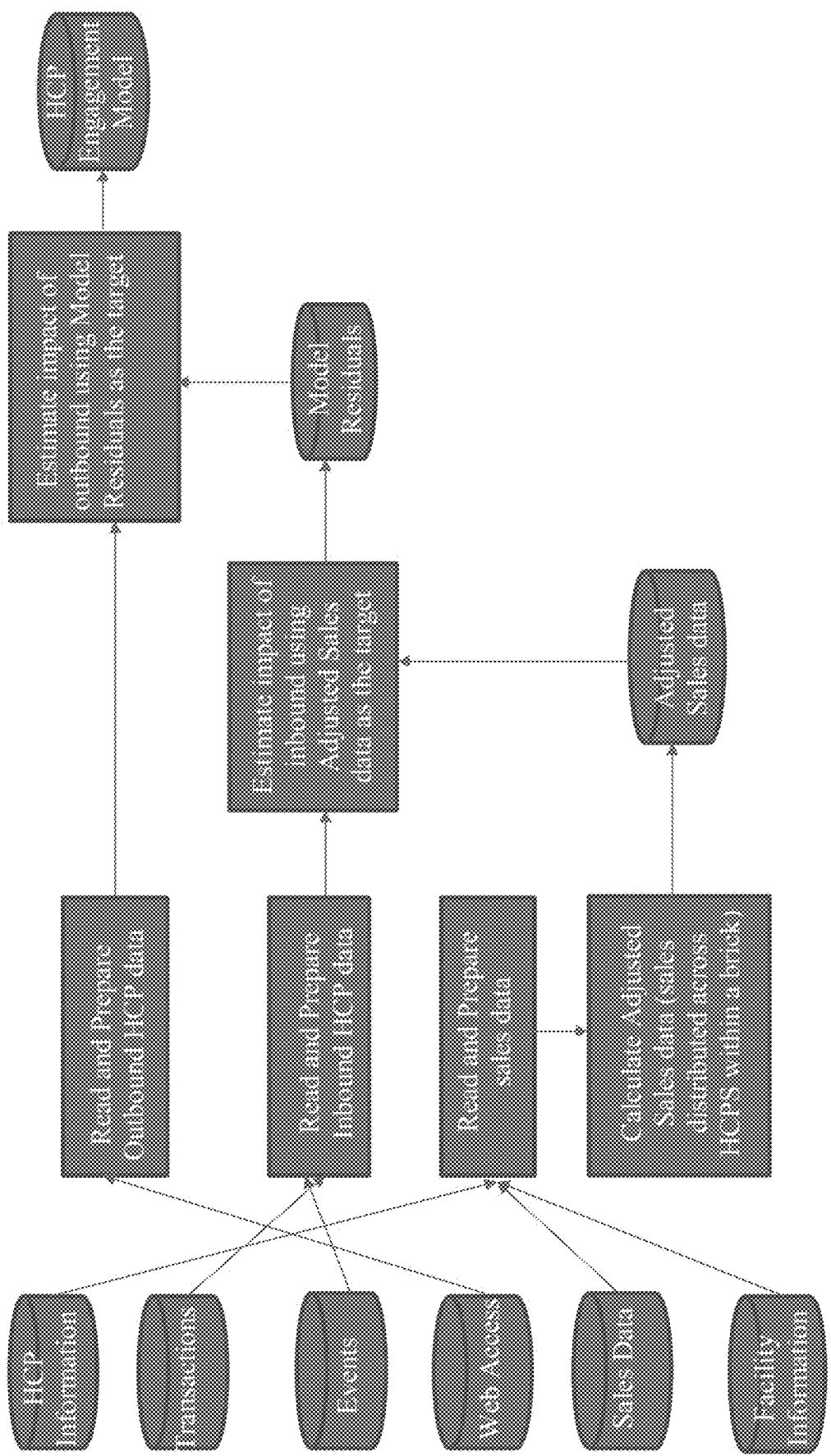
FIG. 6 is a process flow in accordance with some embodiments.

FIG. 6 is a process flow 600 in accordance with some embodiments. In a first step, the system collects data from HCPs and pharma reps, as well as other data that may be provided by CRMs, pharma databases, market segmentation and from other sources. Data collected may include HCP information, transactions, events, web access, sales data, and facility information. The data collected may be stored in the servers, where it may undergo pre-processing in order to be in a suitable format for analysis.

Next, the system reads and prepares unadjusted sales data collected and stored in the servers to form adjusted sales data. The data analyzed for this step may include unadjusted sales data, facility information, and HCP information. The facility information and HCP information may be used to prepare the unadjusted sales data. For example, if it is known, for a particular brick, the origin facility of the sales data within that brick, the brick information may be cross-indexed with the facility and HCP information in order to ascertain which HCPs belong to the facilities with data belonging to the brick. Adjusting the sales data may be performed, for example, using the method of FIG. 3 (distributing the sales across HCPs within a brick).

Next, the system reads and prepares inbound HCP data. Data collected may include data on events and transactions. Event data may include inbound actions taken by the pharma rep towards HCPs in order to market goods and services to the HCPs who write prescriptions for their patients who in turn may make a purchase to fulfill the prescriptions. Transaction data may include records of the following. In the US, the data may be collected at pharmacies and other distributors of drugs as to which prescriptions were filled and the HCPs that ordered them (such data may be collected by IQVIA, as an example). In other regions such as Europe, the data on HCP script writing may be generally not available except at a brick level. In some cases, transaction data may include information on which free samples the sales reps left with an HCP. The pharma reps may also be generally required to record their transaction activity in one or more CRM systems. The system can access the CRM systems, and download the data for processing. The system can convert data into inbound feature information by extracting relevant fields stored within the data and packaging the data into a matrix format. The prepared inbound features are then analyzed using a nonlinear method, for example, as in FIG. 3, in order to remove the effects of the inbound activity data. The system ranks the inbound features based on their estimated effects. The ranking of the inbound features is based on importances or dominances of the individual inbound features. When the function is fit to the adjusted sales data, the system calculates the residuals, which may be analyzed to determine whether any confounding may exist due to the effects of inbound activities. The residuals may be analyzed graphically. A plot of the residuals may be created, and a pattern of residuals within the plot may be analyzed to determine additional confounding. In some embodiments, a new model may be built whereby the residuals are provided as the target to be predicted by the new model.

Next, the system reads and prepares outbound HCP data. Data used for this step may include events and web access data. Event data may include outbound actions taken by HCPs after having communicated with a pharma rep. These actions may be relevant to the product or service discussed by the pharma rep. Web access data may include information on online events attended by the HCP. These online events may include webinars, conferences, talks, training sessions, online expositions, and visits to pharma company web pages. The read and prepared outbound data may then be processed and converted into a matrix format, for analysis by the system. Next, the method may estimate the impact of outbound effects using the model residuals calculated by the inbound processing stage. The method fits a function of the outbound features to the residuals in order to account for the outbound activity effects on HCP engagement. After de-confounding these effects, the system may create an HCP Engagement Model, with inbound and outbound effects accounted for, in order to produce HCP engagement scores.

Figure 7:
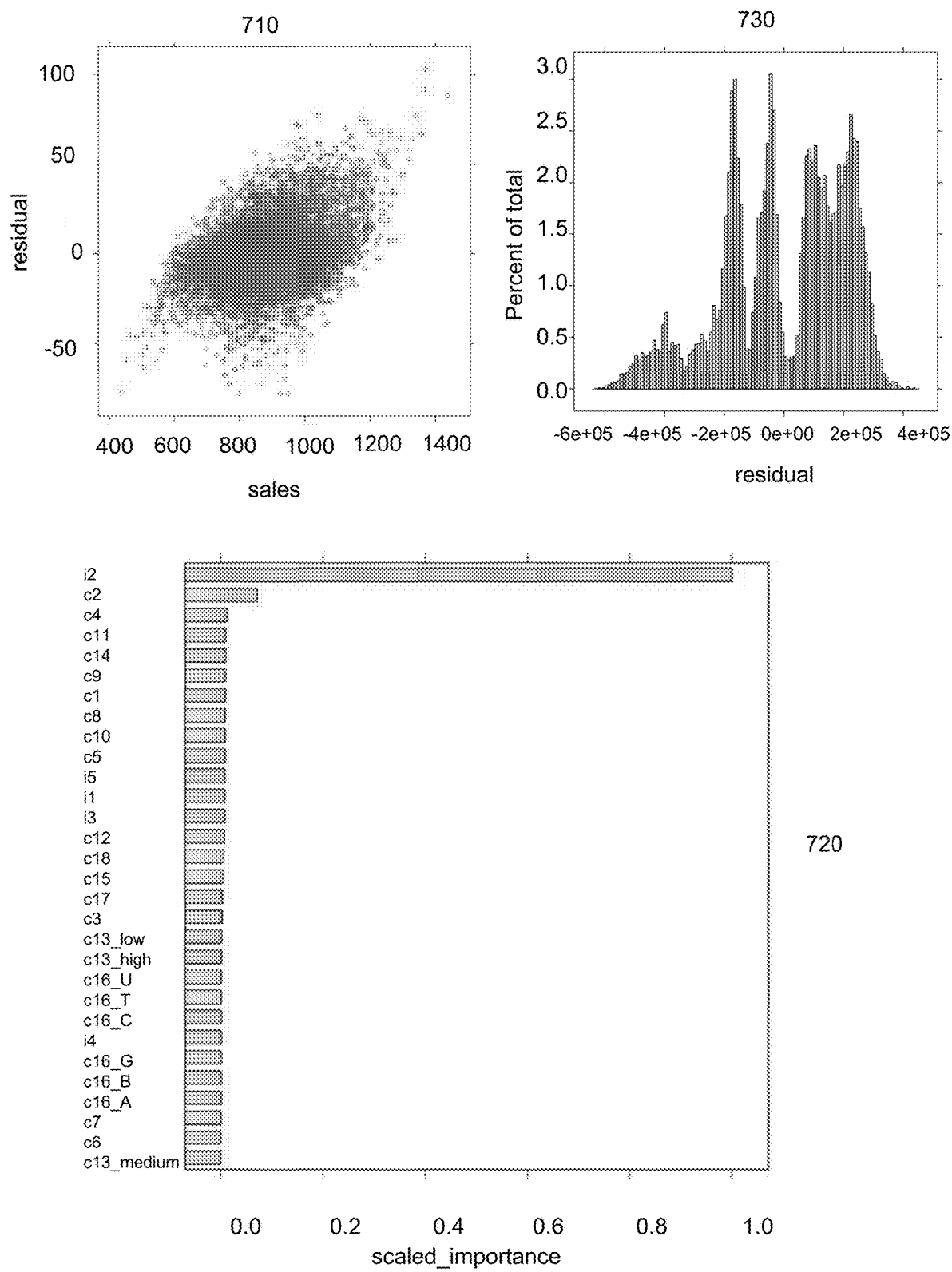
FIG. 7 illustrates visual representations of the process of de-confounding inbound activity effects, in accordance with some embodiments.

FIG. 7 illustrates visual representations of the process of de-confounding inbound activity effects. FIG. 7 shows a residual plot 710, a histogram 730, and a relative importance plot 720.

The relative importance plot 720 shows relative contributions of covariates and inbound features to HCP engagement. For example, there are 30 covariates and inbound features listed in this chart. The relative importance of each feature describes a magnitude of an effect each of the features has on an HCP engagement score. This data was collected during data analysis of the inbound features using the random forest model. Relative importance plots may be constructed using various data analysis tools. The bar chart of the relative importances may be calculated by, for example a random forest code. The relative importance plot 720 shows that the inbound feature i2, having by far the largest relative importance, explained most of the variation in adjusted sales. Effects of the other covariates and inbound features were more minimal. This chart shows that i2 is the most significant predictor that accounts for structure in the residuals. The residual plot 710 shows residuals as functions of adjusted sales. This plot is created based on the residuals determined from the inbound processing stage. The residual plot shows an oval-shaped pattern in the residuals. If the function used to fit inbound features to adjusted sales had captured all of the structure in the relationship between inbound variables and covariates to the adjusted sales, then the residuals would not display a distinct pattern. Because the plots show the oval-shaped pattern, there is an indication that information in the residuals may be associated with the outbound features.

The histogram 730 shows the residuals after the inbound activity effects are compensated for. The graph shows the distribution of the residuals. Since the histogram shows a structure (pattern), this indicates there is remaining information in the residuals that can be modeled to capture additional outbound effects.

Figure 8A:
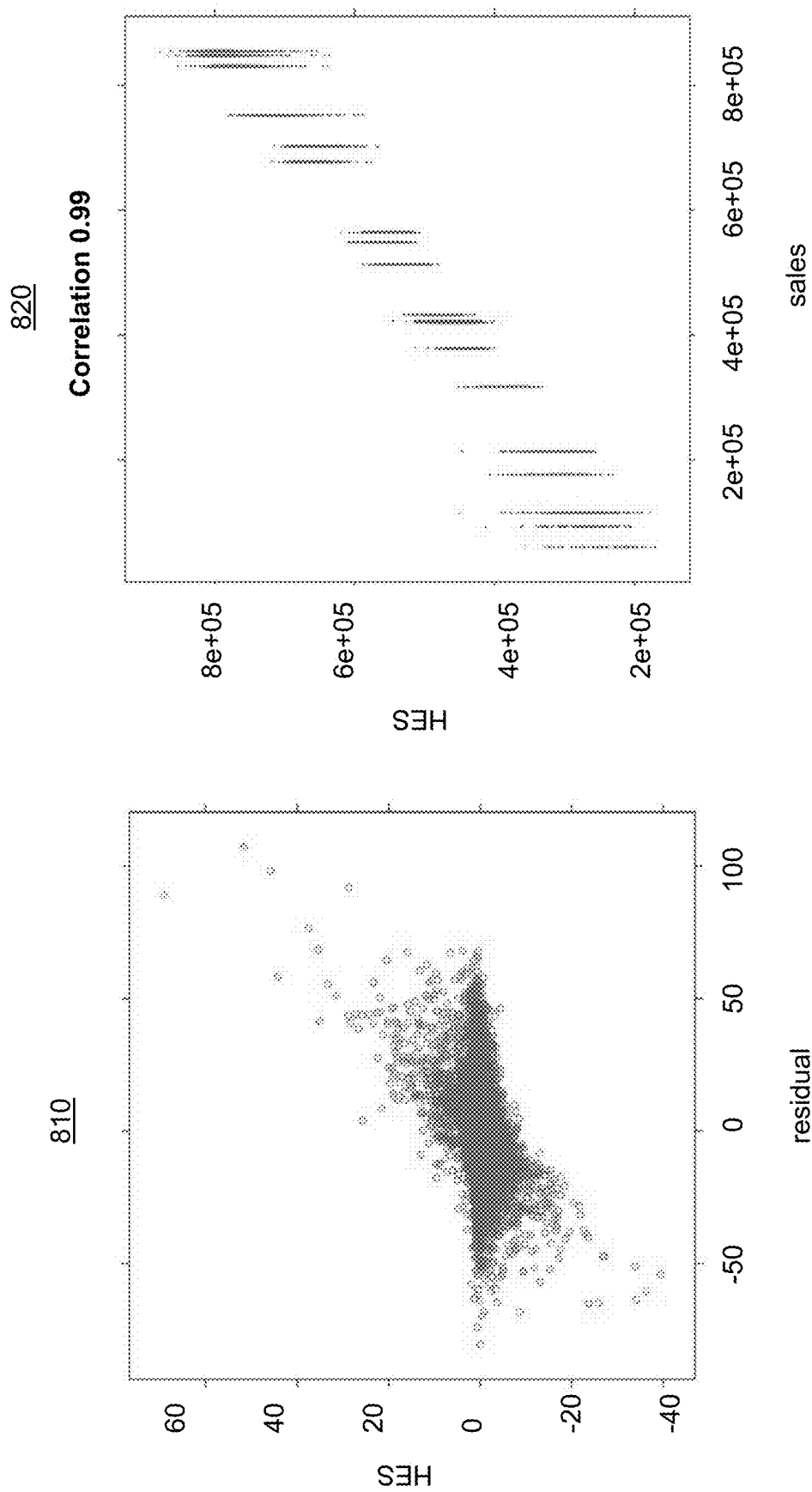
FIG. 8A illustrates visual representations of HCP data after outbound activity effects have been accounted for; [Why highlighted?]

FIG. 8A illustrates visual representations of HCP data after outbound activity effects have been accounted for. FIG. 8A shows a residual plot 810 and a graph 820 showing a relationship between adjusted sales, with outbound activity effects removed, and HES. The visual representations of FIG. 8A show that, after confounding effects have been removed, HES and adjusted sales are highly correlated. This suggests that there is a strong relationship between the pharma reps' targeting behaviors and sales of pharmaceutical products and services.

The graph 820 shows a plot of a correlation between adjusted sales and healthcare engagement score with confounding due to inbound and outbound activities removed. As can be seen, there is a strong correlation between healthcare engagement and adjusted sales when the confounding factors are removed. The graph 820 shows a strong linear association between the two variables. This association implies that actions taken by the pharma reps are directly related to HCP engagement, when confounding factors are removed.

The residual plot 810 illustrates residuals when both the inbound and outbound confounding effects have been removed by the system. The residual plot 810 shows a weaker pattern than that of the residual plot 710 after inbound, but not outbound, effects had been removed. This indicates that confounding effects have been removed. There is still a bimodal pattern in the residuals, indicating some confounding may still be present in the data. The confounding may be due to unknown factors, and may be removed if the system has access to additional data that accounted for those factors.

Figure 8B:
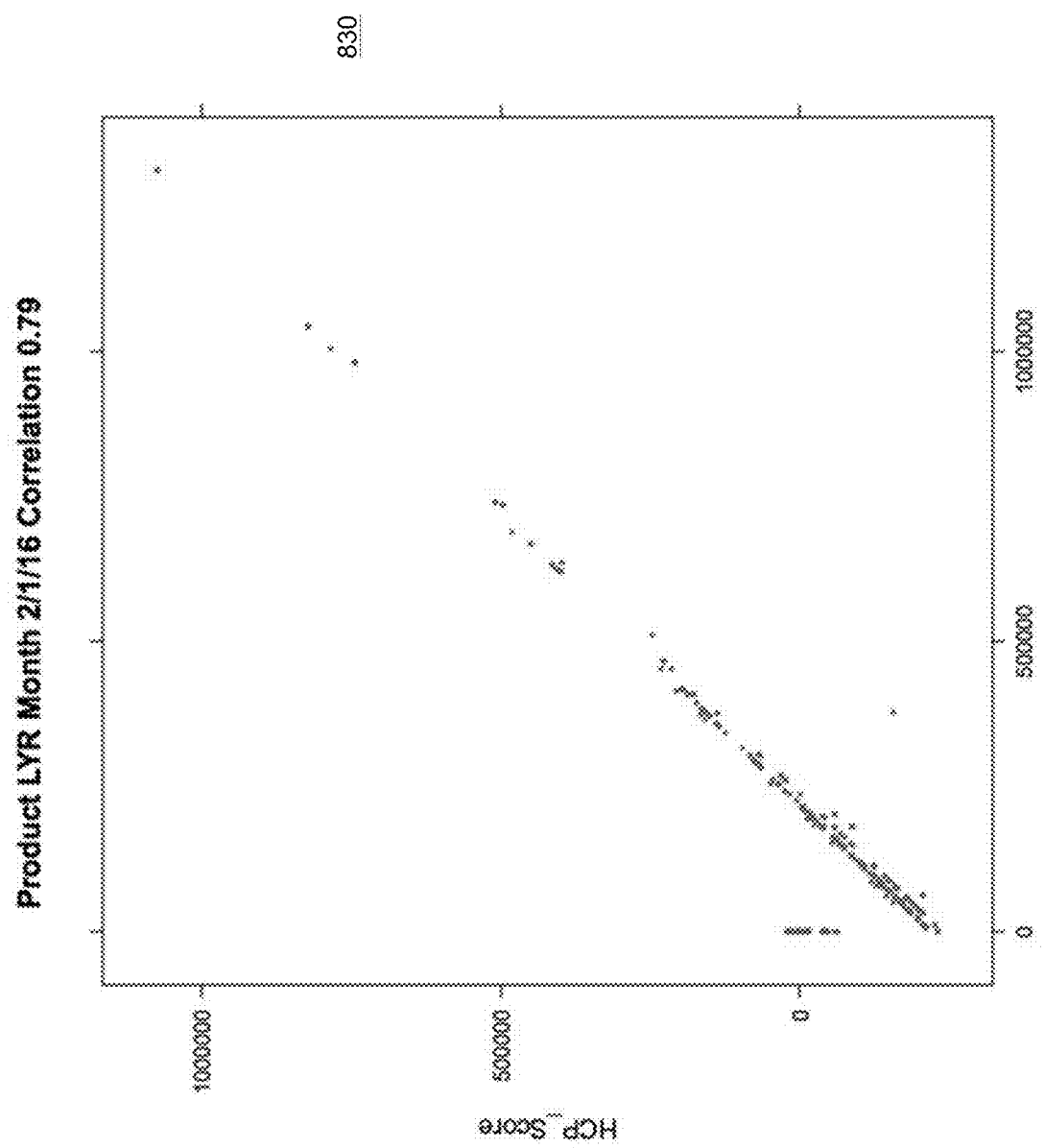
FIG. 8B shows a practical application of a method for reducing the effects of outbound and inbound activity from sales data.

FIG. 8B shows a practical application 830 of the method for reducing outbound and inbound activity. In the example of FIG. 8B, data was collected from 16,722 HCPs over a 36-month period. The covariates were HCP-level demographics. The inbound variables were the number of sends and visits in that month. The outbound variables were the number of logins in that month. The sales are aggregated at the brick level. The results show that, after confounding effects have been removed, that the correlation between HES and sales equaled 0.79.

Computer Systems

Figure 9:
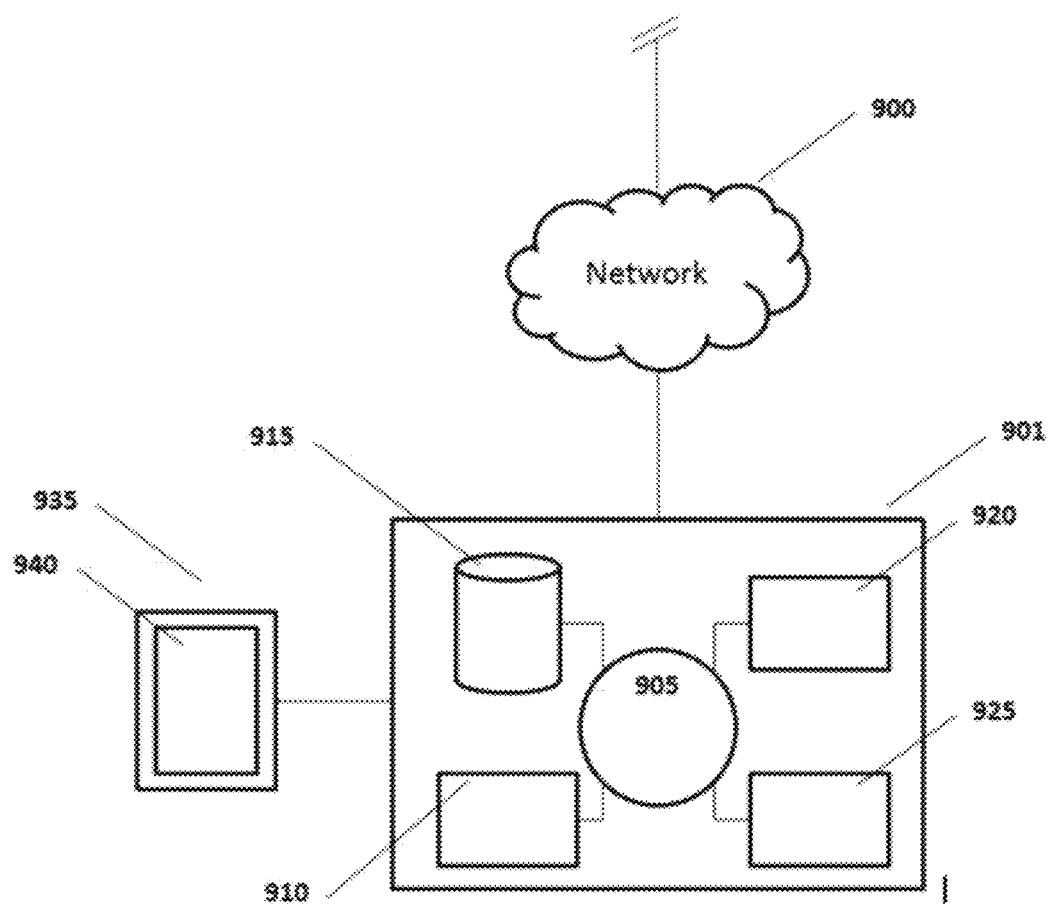
FIG. 9 shows a computer system that is programmed or otherwise configured to perform data sharing and analysis tasks, in accordance with the embodiments disclosed herein.

The present disclosure provides computer systems that are programmed to implement methods of the disclosure. FIG. 9 shows a computer system 901 that is programmed or otherwise configured to perform data sharing and analysis tasks. The computer system 901 can regulate various aspects of the present disclosure, such as, for example, storing actions from HCPs and pharma reps and performing machine learning analysis. The computer system 901 can be an electronic device of a user or a computer system that is remotely located with respect to the electronic device. The electronic device can be a mobile electronic device.

The computer system 901 includes a central processing unit (CPU, also "processor" and "computer processor" herein) 905, which can be a single core or multi core processor, or a plurality of processors for parallel processing. The computer system 901 also includes memory or memory location 910 (e.g., random-access memory, read-only memory, flash memory), electronic storage unit 915 (e.g., hard disk), communication interface 920 (e.g., network adapter) for communicating with one or more other systems, and peripheral devices 925, such as cache, other memory, data storage or electronic display adapters. The memory 910, storage unit 915, interface 920 and peripheral devices 925 are in communication with the CPU 905 through a communication bus (solid lines), such as a motherboard. The storage unit 915 can be a data storage unit (or data repository) for storing data. The computer system 901 can be operatively coupled to a computer network ("network") 930 with the aid of the communication interface 920. The network 930 can be the Internet, an internet or extranet, or an intranet or extranet that is in communication with the Internet. The network 930 in some cases is a telecommunication or data network. The network 930 can include one or more computer servers, which can enable distributed computing, such as cloud computing. The network 930, in some cases with the aid of the computer system 901, can implement a peer-to-peer network, which may enable devices coupled to the computer system 601 to behave as a client or a server.

The CPU 905 can execute a sequence of machine-readable instructions, which can be embodied in a program or software. The instructions may be stored in a memory location, such as the memory 910. The instructions can be directed to the CPU 905, which can subsequently program or otherwise configure the CPU 905 to implement methods of the present disclosure. Examples of operations performed by the CPU 905 can include fetch, decode, execute, and writeback.

The CPU 905 can be part of a circuit, such as an integrated circuit. One or more other components of the system 901 can be included in the circuit. In some cases, the circuit is an application specific integrated circuit (ASIC).

The storage unit 915 can store files, such as drivers, libraries and saved programs. The storage unit 915 can store user data, e.g., user preferences and user programs. The computer system 901 in some cases can include one or more additional data storage units that are external to the computer system 901, such as located on a remote server that is in communication with the computer system 901 through an intranet or the Internet.

The computer system 901 can communicate with one or more remote computer systems through the network 930. For instance, the computer system 901 can communicate with a remote computer system of a user. Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 901 via the network 930.

Methods as described herein can be implemented by way of machine (e.g., computer processor) executable code stored on an electronic storage location of the computer system 901, such as, for example, on the memory 910 or electronic storage unit 915. The machine executable or machine readable code can be provided in the form of software. During use, the code can be executed by the processor 905. In some cases, the code can be retrieved from the storage unit 915 and stored on the memory 910 for ready access by the processor 605. In some situations, the electronic storage unit 915 can be precluded, and machine-executable instructions are stored on memory 910.

The code can be pre-compiled and configured for use with a machine having a processer adapted to execute the code, or can be compiled during runtime. The code can be supplied in a programming language that can be selected to enable the code to execute in a pre-compiled or as-compiled fashion.

Aspects of the systems and methods provided herein, such as the computer system 901, can be embodied in programming. Various aspects of the technology may be thought of as "products" or "articles of manufacture" typically in the form of machine (or processor) executable code or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code or data. Many of these forms of computer readable media may be involved in carrying one or more sequences of one or more instructions to a processor for execution.

The computer system 901 can include or be in communication with an electronic display 935 that comprises a user interface (UI) 940 for providing, for example, recommended actions to a pharma rep. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 905. The algorithm can, for example, be a machine learning algorithm used to generate a message recommendation.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A computer-implemented method for generating adjusted sales data, the method comprising:

periodically obtaining data from a plurality of data sources, wherein the data comprises (1) aggregate sales values of a pharmaceutical product and (2) a plurality of attributes comprising (i) information associated with a plurality of healthcare facilities and (ii) information associated with a plurality of healthcare providers (HCPs), wherein the plurality of HCPs is provided under a plurality of bricks with each brick comprising one or more of the healthcare facilities and each facility comprising one or more HCPs;

monitoring, via a server having one or more processors, outbound activity data from a plurality of electronic devices of the plurality of HCPs;

generating, based on the monitoring and by one or more processors, outbound matrix representing the outbound activity data of the plurality of HCPs, wherein the outbound activity matrix comprises (1) a plurality of outbound features as columns in the matrix and (2) the individual HCPs in the brick as rows in the matrix;

generating the adjusted sales data by distributing the aggregate sales values across the HCPs that are within each brick for the plurality of bricks based on (1) a pseudoinverse of the outbound matrix and (2) an average brick level sales per HCP in the brick;

executing, by one or more processors, a machine learning algorithm, to fit a function of inbound activity data and covariates to the adjusted sales data, wherein fitting the function comprises applying a plurality of weights to the inbound activity data, wherein a weight of the plurality of weights corresponds to a relative importance of an inbound activity to the adjusted sales data; and responsive to retrieving additional data from the plurality of data sources, adjusting by the machine learning algorithm, one or more weights of the plurality of weights.

2. The method of claim 1, wherein the plurality of data sources comprises multiple databases for customer resource management (CRM), market segmentation, sales, and/or a pharmaceutical company's proprietary databases.

3. The method of claim 1, wherein the plurality of bricks is defined based on one or more factors including geographical region, location of a facility, size of a facility, number of HCPs within a facility, socioeconomics of a region, demographics of a region, or other non-geographical factor(s).

4. The method of claim 1, wherein the plurality of bricks comprises a first group of bricks and a second group of bricks, wherein each brick in the first group of bricks comprises a distinct collection of healthcare facilities, and wherein each brick in the second group of bricks comprises a single distinct healthcare facility.

5. The method of claim 1, wherein the adjusted sales data comprises sales values that are disaggregated at an individual HCP level instead of at a brick level.

6. The method of claim 1, further comprising:
using the adjusted sales data as a target in a predictive model to estimate impacts of different marketing strategies on the sales of the pharmaceutical product.

7. The method of claim 6, further comprising:
identifying, based on the estimated impacts of the different marketing strategies, one or more marketing strategies to optimize the sales of the pharmaceutical product.

8. The method of claim 7, further comprising:
providing recommendations of the one or more identified marketing strategies to a user, wherein the user includes one or more sales representatives for the pharmaceutical product.

9. The method of claim 8, wherein the recommendations are provided as one or more graphical visual objects configured to be displayed on an electronic device associated with the user.

10. The method of claim 1, wherein the outbound activity data is associated with one or more actions taken by the HCPs that are not a direct result of specific actions taken by an entity that is selling the pharmaceutical product.

11. The method of claim 10, wherein the plurality of outbound features comprises (1) a number of visits by the HCPs to webpages of a company that is offering the pharmaceutical product for sale, (2) a number of communications from the HCPs to one or more sales representatives for the pharmaceutical product, (3) a number of relevant symposiums attended by the HCPs, or (4) a number of endorsements by the HCPs of the pharmaceutical product or other similar HCP actions.

12. The method of claim 11, wherein a subset of the plurality of outbound features is functions of, or related to each other.

13. The method of claim 11, wherein a subset of the plurality of outbound features are functions of, or related to one or more of the attributes.

14. The method of claim 1, wherein the aggregate sales values are distributed across the HCPs within each brick by projecting the aggregate sales values onto a space defined by the outbound activity.

15. The method of claim 14, wherein the aggregate sales values are projected onto the space using a linear transformation or a non-linear transformation.

16. The method of claim 1, wherein a plurality of weights is applied to the plurality of outbound features associated with the outbound activity, wherein a higher weight is applied to a first outbound feature having a higher value or importance, and a lower weight is applied to a second outbound feature having a lower value or importance.

17. The method of claim 16, further comprising adjusting the plurality of weights based on reevaluating the significance of the plurality of outbound features.

18. The method of claim 1, wherein the plurality of outbound features comprises a quantity of hyperlink clicks in messages to the HCPs.

19. A system for generating adjusted sales data, the system comprising:
a server in communication with a plurality of data sources; and
a memory storing instructions that, when executed by the server, cause the server to perform operations comprising:
periodically obtaining data from the plurality of data sources, wherein the data comprises (1) aggregate sales values of a pharmaceutical product and (2) a plurality of attributes comprising (i) information associated with a plurality of healthcare facilities and (ii) information associated with a plurality of healthcare providers (HCPs), wherein the plurality of HCPs is provided under a plurality of bricks with each brick comprising one or more of the facilities and each facility comprising one or more HCPs;
monitoring, via a server having one or more processors, outbound activity data from a plurality of electronic devices of the plurality of HCPs;
generating, based on the monitoring and by one or more processors, outbound matrix representing the outbound activity data of the plurality of HCPs, wherein the outbound activity matrix comprises (1) a plurality of outbound features as columns in the matrix and (2) the individual HCPs in the brick as rows in the matrix;
generating the adjusted sales data by distributing the aggregate sales values across the HCPs that are within each brick for the plurality of bricks based on (1) a pseudoinverse of the outbound matrix and (2) an average brick level sales per HCP in the brick;
executing, by one or more processors, a machine learning algorithm, to fit a function of inbound activity data and covariants to the adjusted sales data, wherein fitting the function comprises applying a plurality of weights to the inbound activity data, wherein a weight of the plurality of weights corresponds to a relative importance of an inbound activity to the adjusted sales data; and responsive to retrieving additional data from the plurality of data sources, adjusting by the machine learning algorithm, one or more weights of the plurality of weights.

20. A non-transitory computer-readable storage medium including instructions that, when executed by a server, cause the server to perform operations comprising:

periodically obtaining data from a plurality of data sources, wherein the data comprises (1) aggregate sales values of a pharmaceutical product and (2) a plurality of attributes comprising (i) information associated with a plurality of healthcare facilities and (ii) information associated with a plurality of healthcare providers (HCPs), wherein the plurality of HCPs is provided under the plurality of bricks with each brick comprising one or more of the healthcare facilities and each facility comprising one or more HCPs;

monitoring, via a server having one or more processors, outbound activity data from a plurality of electronic devices of the plurality of HCPs;

generating, based on the monitoring and by one or more processors, outbound matrix representing the outbound activity data of the plurality of HCPs, wherein the outbound activity matrix comprises (1) a plurality of outbound features as columns in the matrix and (2) the individual HCPs in the brick as rows in the matrix;

generating the adjusted sales data by distributing the aggregate sales values across the HCPs that are within each brick for the plurality of bricks based on (1) a pseudoinverse of the outbound matrix and (2) an average brick level sales per HCP in the brick;

executing, by one or more processors, a machine learning algorithm, to fit a function of inbound activity data and covariates to the adjusted sales data, wherein fitting the function comprises applying a plurality of weights to the inbound activity data, wherein a weight of the plurality of weights corresponds to a relative importance of an inbound activity to the adjusted sales data; and responsive to retrieving additional data from the plurality of data sources, adjusting, by the machine learning algorithm, one or more weights of the plurality of weights.

21. A computer-implemented method for generating adjusted sales data, the method comprising:

periodically obtaining data from a plurality of data sources, wherein the data comprises (1) aggregate sales values of a pharmaceutical product and (2) a plurality of attributes comprising (i) information associated with a plurality of healthcare facilities and (ii) information associated with a plurality of healthcare providers (HCPs), wherein the plurality of HCPs is provided under a plurality of groups with each group comprising one or more of the healthcare facilities and each facility comprising one or more HCPs;

monitoring, via a server having one or more processors, outbound activity data from a plurality of electronic devices of the plurality of HCPs;

generating, based on the monitoring and by one or more processors, outbound matrix representing the outbound activity data of the plurality of HCPs, wherein the outbound activity matrix comprises (1) a plurality of outbound features as columns in the matrix and (2) the individual HCPs in the group as rows in the matrix; and generating the adjusted sales data by distributing the aggregate sales values across the HCPs that are within each group for the plurality of groups based on (1) a pseudoinverse of the outbound matrix and (2) an average group level sales per HCP in the group;

executing, by one or more processors, a machine learning algorithm, to fit a function of inbound activity data and covariates to the adjusted sales data, wherein fitting the function comprises applying a plurality of weights to the inbound activity data, wherein a weight of the plurality of weights corresponds to a relative importance of an inbound activity to the adjusted sales data; and responsive to retrieving additional data from the plurality of data sources, adjusting by the machine learning algorithm, one or more weights of the plurality of weights.

* * * * *